Figure 1:
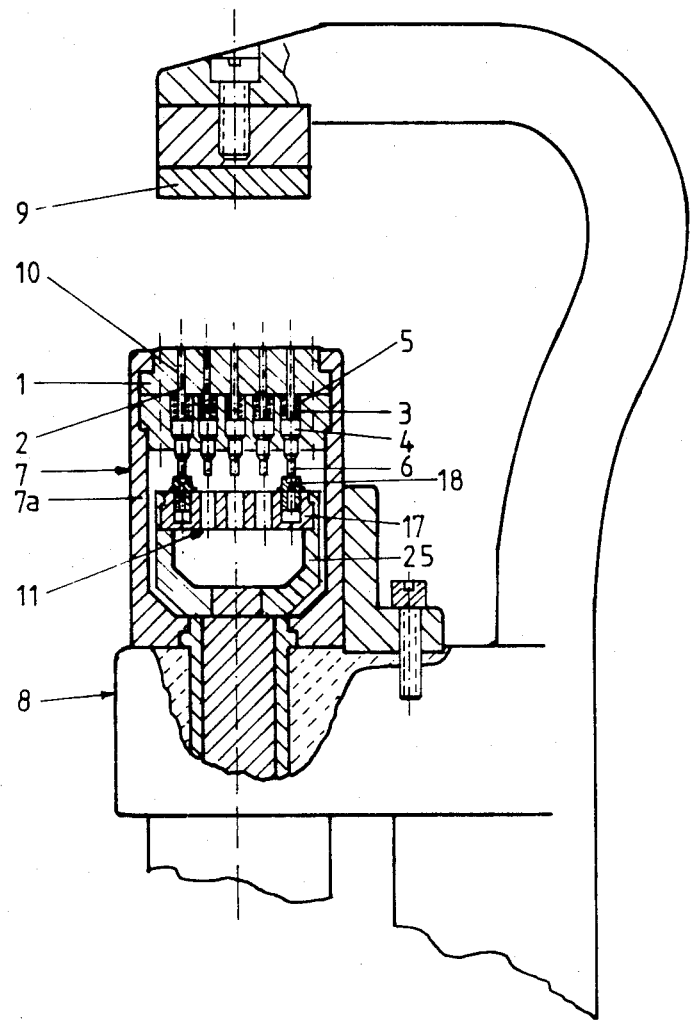

United States Patent [19]

Niemeijer

[11] Patent Number: 4,488,550
[45] Date of Patent: Dec. 18, 1984

[54] TATTOOING DEVICE AND PROGRAM CARRIER THEREFORE

[75] Inventor: Halbe J. Niemeijer, Bruntinge, Netherlands

[73] Assignee: Dawsonville Corporation N.V., Netherlands

[21] Appl. No.: 399,329

[22] Filed: Jul. 19, 1982

[30] Foreign Application Priority Data

Jul. 21, 1981 [NL] Netherlands .................. 8103433

[51] Int. Cl.³ .................. A61D 1/00; B44B 5/00; B43K 5/00
[52] U.S. Cl. .................. 128/316; 81/9.22; 101/26; 101/19; 40/300
[58] Field of Search .................. 128/316, 330, 329 A, 128/154, 315, 324, 333; 81/9.22; 101/24, 26, 30, 19; 40/300; 604/51, 73, 310–311, 890–891, 139, 201–206

[56] References Cited

U.S. PATENT DOCUMENTS

| | | | |
|---|---|---|---|
| 1,851,672 | 3/1932 | Ker | 101/26 |
| 2,175,365 | 10/1939 | Saffir | 604/202 |
| 2,627,856 | 2/1953 | Waterman | 604/203 |
| 2,864,364 | 12/1958 | Mizzy | 604/203 |
| 3,605,744 | 9/1971 | Dwyer | 604/51 |
| 4,214,490 | 7/1980 | Chizek | 101/26 |
| 4,230,001 | 10/1980 | Noll | 101/26 |
| 4,286,599 | 9/1981 | Hahn | 128/316 |
| 4,392,493 | 7/1983 | Niemeijer | 128/316 |

FOREIGN PATENT DOCUMENTS 6395 1/1980 European Pat. Off. ............ 81/9.22

Primary Examiner—C. Fred Rosenbaum
Assistant Examiner—Gene B. Kartchner
Attorney, Agent, or Firm—Andrus, Sceales, Starke & Sawall

[57] ABSTRACT

A tattooing device comprises a needle carrier (1) having a plurality of hollow needles (2), an exchangeable program carrier (11,26,31,39) and control means having a jaw (7). The program carrier has an assembly of cylindrical cavities (13,28,33,40) with a fluid (23), each of which can be put into open communication with a needle, in which cavities pistons (6,18,34,38) are movable for pressing out the fluid and which cavities are at least partly closed at an axial end by a closing element (18,29,34,41) in dependence on the force exerted by the jaw for transfer to the needle. The closing element is at least partly deformable, the deformation of the closing element requiring a heavier force than that required for inserting the needle into the tissue so that owing to the force exerted by the jaw on the program carrier first the needle is inserted into the tissue and subsequently by the deformation of the closing element the piston can move into the cavity.

12 Claims, 7 Drawing Figures

TATTOOING DEVICE AND PROGRAM CARRIER THEREFORE

The invention relates to a tattooing device comprising a needle carrier supporting a plurality of hollow needles, an exchangeable program carrier having a contrast fluid reservoir and control means with a jaw being coupable with the needle carrier and the program carrier in order to exert a force on said carriers to drive needles relatively arranged in accordance with a symbol into the tissue to be tattooed and to press contrast fluid out of the reservoir through the needles into the tissue.

A tattooing device of the kind set forth is known from European patent application No. 80200830 of the Applicant corresponding to U.S. Pat. No. 4,392,493 issued July 12, 1983. In this known tattooing device the needles selected by the program carrier from a needle matrix are provided with fluid from one reservoir. The jaw of this known device has two separate elements, one of which co-operates with the needle carrier and the other with the program carrier. In order to ensure that the fluid is not added until the needles have been inserted it is necessary in the known device to energize the second pressing element only after the first pressing element has been energized. For this purpose the known device comprises a specific coupling mechanism which ensures that the two pressing elements are energized in said order of succession by the control means. This coupling mechanism renders the known device rather complicated.

The invention has for its object to provide a tattooing device of kind set forth in which the said order of succession of inserting the needles and feeding contrast fluid is reliably ensured by using a simple jaw construction, whilst moreover each needle receives the correct amount of fluid.

According to the invention the program carrier comprises an assembly of cylindrical cavities, each cavity forming a fluid reservoir and being adapted to be placed into open communication with a needle, in which cavity a piston is movable for pressing out the fluid, said cavity being at least partly closed at an axial end by a closing element initially for transferring the force exerted by the jaw to the needle, said closing element being at least partly deformable, the deformation of the closing element requiring a heavier force than that required for driving the needle into the tissue so that owing to the force exerted by the jaw on the program carrier first the needle is driven into the tissue and subsequent to the deformation of the closing element the piston is movable into the cavity for pressing out the fluid.

In this manner a tattooing device is obtained, in which the order of succession of the insertion of the needles and the addition of fluid is mainly determined by the construction of the program carrier. This two-step operation of the device embodying the invention is particularly obtained by the use of the deformable closing element of the program carrier, which permits the addition of fluid only after a given force is exerted on the program carrier. When a weaker force is exerted on the program carrier, only the needles are inserted into the tissue. By providing a selected number of cavities of the program carrier with fluid the symbol to be tattooed can be simply determined in advance in the program carrier, whilst it is in addition possible to feed a metered amount of fluid into each needle in tattooing.

A preferred embodiment of a tattooing device in accordance with the invention is characterized in that the program carrier comprises in addition a plurality of cavities not provided with a closing element and being fully open at said axial end. By this construction of the program carrier it is ensured that the non-selected needles can move by their first end parts freely into the program carrier and will, therefore, not penetrate into the tissue by their opposite free ends. It is thus avoided that redundant tissue perforations should be made. A further preferred embodiment of a tattooing device in accordance with the invention is characterized in that the closing element is formed by a piston located at least partly in the cavity and being connectable with a needle, said piston having an internal fluid channel and having externally a deformable peripheral element, by which the piston is initially coupled with an axial end of the cavity during the insertion of the needle into the tissue, which peripheral element is movable into the cavity owing to the force exerted by the jaw for pressing out the fluid. In this way the piston provides both the said two-step effect and a pump effect for pressing out the fluid.

In connection herewith a further preferred embodiment of a device in accordance with the invention, the program carrier of which can be manufactured in a simple manner, is characterized in that the piston initially forms an integral part of the program carrier and is connected only by the peripheral element with the axial end of the cavity, said connection being interrupted by the force exerted by the jaw. Therefore, the piston can be formed simultaneously with the program carrier by spray casting a synthetic resin.

A further preferred embodiment of a device in accordance with the invention is characterized in that the assembly of cylindrical cavities is closed at an axial end by a foil. Thus the cavities provided with a fluid can be readily closed at said end.

In this connection a two-step effect is obtained in a very simple manner when the closing element is formed by the foil.

Figure 2:
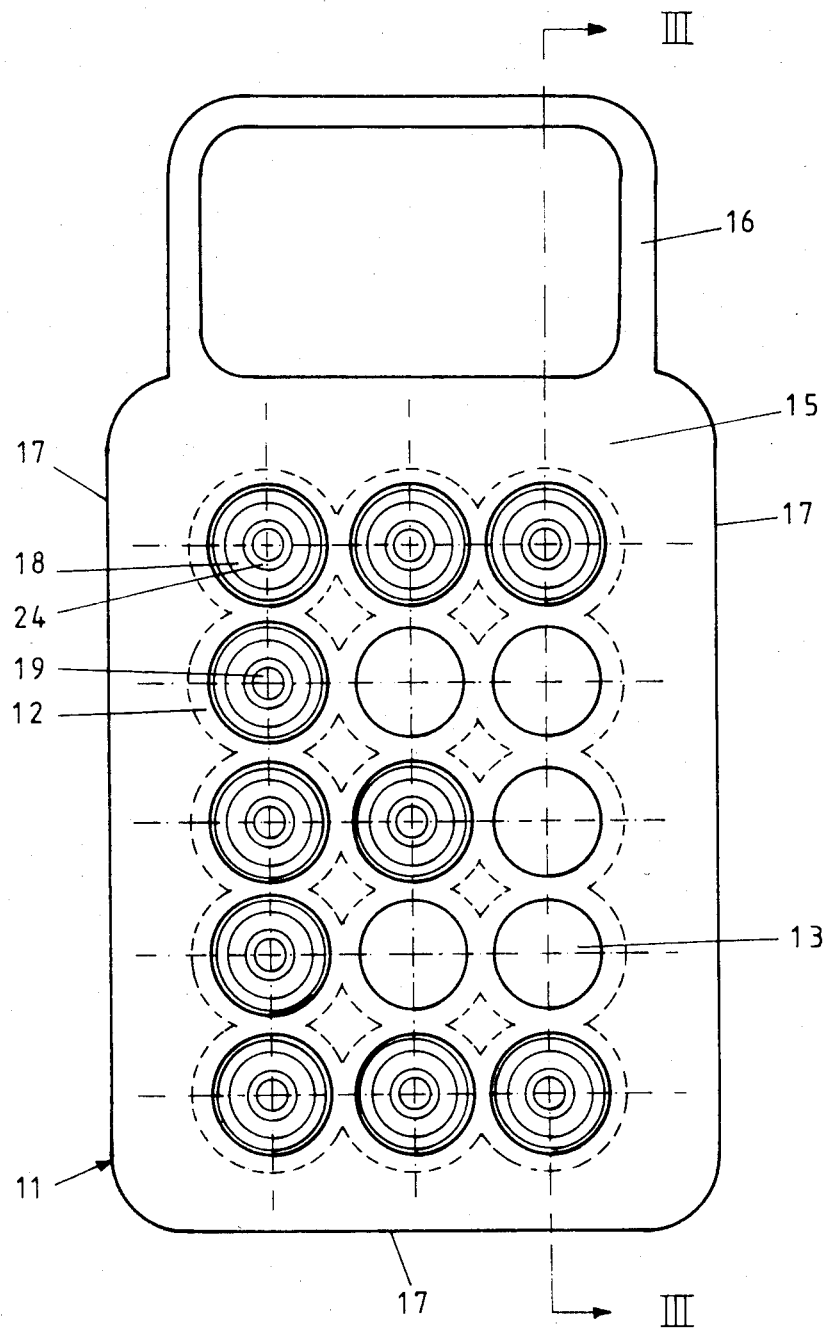
Figure 3:
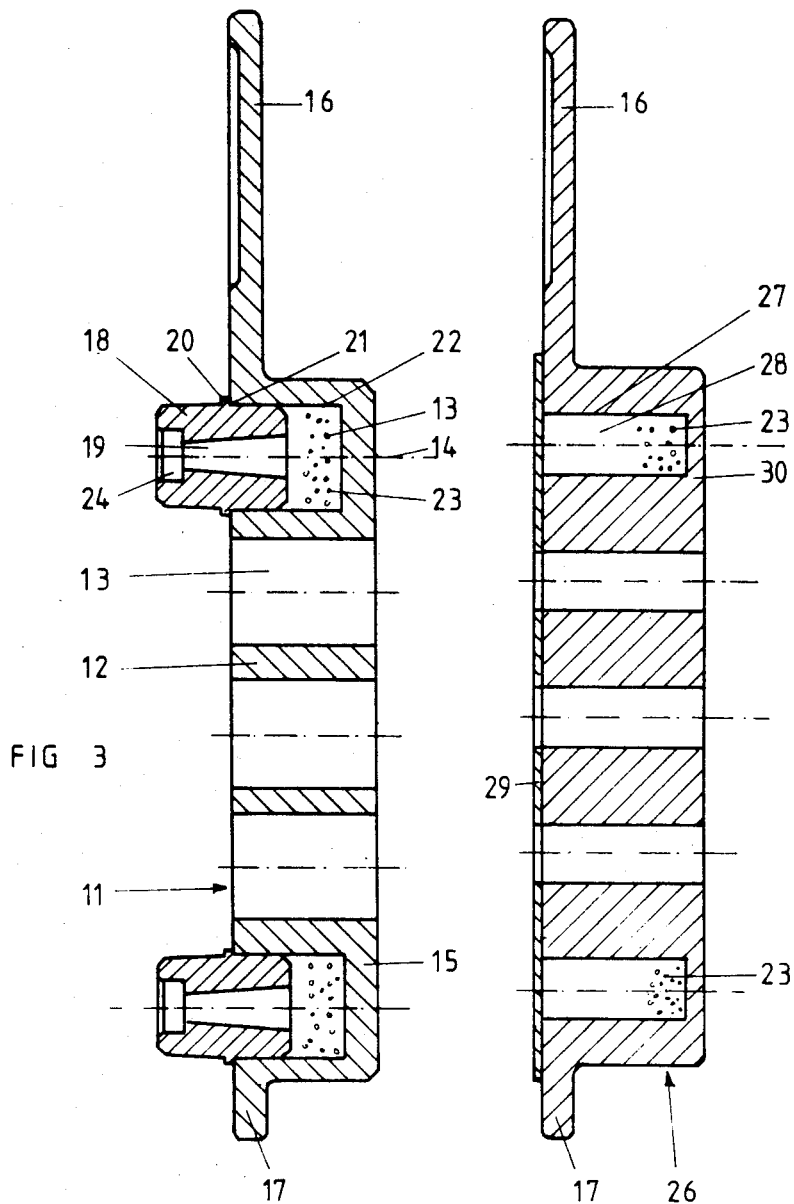

The invention will be described more fully with reference to several embodiments shown in the drawing, to which, however, the invention is not limited. The drawing shows in FIG. 1 partly an elevational view and partly a sectional view of part of a tattooing device embodying the invention, FIG. 2 an enlarged plan view of a program carrier of the device of FIG. 1, comprising a plurality of pistons, FIG. 3 a sectional view taken on the lines III—III in FIG. 2, FIG. 4 a sectional view of a program carrier of a second embodiment of a device in accordance with the invention, FIG. 5 a sectional view of a program carrier of a third embodiment of a device in accordance with the invention, FIG. 6 a sectional view of part of a fourth embodiment of a device in accordance with the invention, FIG. 7 a sectional view of part of a program carrier in the device of FIG. 6 on an enlarged scale.

The tattooing device illustrated in FIG. 1 comprises a needle carrier 1 having an assembly of hollow needles 2 arrayed in a matrix. In this embodiment a 3×5 matrix is available for each symbol, but other matrices are also possible. The needles 2 are retained in a drawn-in position by compression springs 3 engaging thickened parts 4 of the needls and an inner wall 5 of the carrier 1, in which end or coupling parts 6 of the needles 2 protrude out of the carrier 1. The carrier 1 is fastened to a sliding piece 7a of a jaw or bit 7 forming part of control means constituted by pincers 8 shown only partly in FIG. 1. The sliding piece 7a is rectilinearly moveable with respect to a jaw 9 of the pincers 8, said jaw being intended to support the tissue to be tattooed on the side remote from the needles 2.

The needle carrier 1 has channels 10 accommodating the needles in a manner such that, when a force is exerted on the needle in the direction of length, the needle will be displaced inside the channel 10 against the force of the spring 3. Inside the sliding piece 7a space is available for accommodating a program carrier 11. As is shown in detail in FIGS. 2 and 3, the carrier 11 comprises an assembly of tubular elements 12 arrayed in this embodiment also in a 3×5 matrix. The elements 12 have each a cylindrical cavity 13, the centre line 14 of which registers with the centre line of the associated needle 2 after the carrier 11 is arranged in the pincers 8. The assembly of elements 12 are integral with a base plate 15 and a handle 16 and are preferably manufactured in a single run from an appropriate synthetic resin by spray casting, for example, from polypropylene.

The edges 17 of the plate 15 constitute positioning means for the carrier 11 with respect to the jaw 7 of the pincers 8. In the carrier a plurality of cavities 13 relatively arranged in accordance with a programmed symbol—in FIG. 2 the number 3 is shown by way of example—are completely closed at one end by the presence of the base plate 15. At the other axial end these cavities are limited each by a closing element located at least partly in the cavity and formed by a piston 18. Each piston 18 has an inner fluid channel 19 and is provided on the outer side with a peripheral element formed by a continuous shoulder 20. In order to facilitate the introduction into the cavity the outer wall of the piston 18 may be slightly tapering up to the shoulder 20. In the engaged position of the program carrier 11 shown in FIG. 3 the piston is in contact by the shoulder 20 with an upper edge 21 of the cavity 13. The disposition of the shoulder 20 with respect to the edge 21 and the choice of the synthetic resin employed are such that, when a given force is exerted on the piston 18 in a manner to be discussed hereinafter, the shoulder is slightly deformed and pressed into the cavity 13.

In this way a plurality of cavities 13 enclose reservoirs 22 into which, after the manufacture of the carrier 11, a preferably pastelike contrast fluid 23 is introduced. The fluid 23 is locked in the reservoir 22 in a manner such that, when the piston 18 is moved after deformation of the shoulder 20 into the cavity 13 towards the base plate 15, the piston exerts pressure on the fluid 23. Owing to this pressure the fluid 23 can flow through the channel 19 towards the other side of the piston. Since the outer wall of the piston has a cylindrical shape away from the shoulder 20, no fluid can escape between the piston wall and the wall of the cavity.

Each piston 18 has a recess 24 adjoining the channel 19 and having a diameter exceeding that of the channel, which recess can be coupled with the coupling part 6 of the needle 2. In order to provide a satisfactory seal between the coupling part and the piston, the recess 24 may, if necessary, have a shape, as the case may be, conically narrowing towards the channel 19.

The cylindrical cavities 13 of the elements not provided with a piston are not covered by the base plate 15 and are thus fully open at both axial ends. In the manufacture of the carrier 11 this can be achieved by punching out the bottom out of a number of cavities 13 in dependence on the symbol to be programmed. Since the diameter of the cavities is slightly larger than that of the coupling parts 6 of the needles 2, the needles with the coupling parts can move through the carrier in the non-closed cavities.

For preparing the tattooing device a program carrier 11 composed in accordance with the desired, programmed symbol is placed in a printing element 25. The printing element constitutes the active part of the jaw 7 and is located inside the sliding piece 7a. After the insertion the carrier 11 is located by its edges in positioning grooves of the printing element 25. Subsequently, when the pincers 8 are actuated by the printing element 25, the program carrier is displaced towards the needle carrier 1, the recesses 24 of the pistons 18 coupling with a coupling part 6 of the selected needles 2. By the pressure of the printing element 25 on the carrier 11 a force is exerted on the needles 2 through the pistons 18. Owing to the force on the needles and hence on the needle carrier the sliding piece 7a is displaced up to a stop (not shown) in the pincers 8. The pressure of the element 25 is sufficiently high to cause the needles 2 disposed in accordance with the programmed symbol to move by the free ends against the force of the compression springs 3 out of the needle carrier and to subsequently penetrate into the tissue. Thus tissue perforations are formed. The further needls registering with cavities 13 not provided with a piston move through the carrier 11 with the coupling part 6 and thus remain in a withdrawn position in the needle carrier 1. In this way those needles remain inoperative.

Subsequently a higher force is exerted on the program carrier 11 by the pressure element 25, said force, as stated above, resulting in each shoulder moving thrustwise in a cavity 13. Owing to the abrupt movement of the piston 18 a high pressure is exerted for a short time on the fluid 23. Since, moreover, each channel 19 has a shape conically narrowing towards the needle, the fluid stream is accelerated in the direction of the needle so that it is ensured that the fluid can readily flow through the needle into the tissue perforation. Thus the tattooing device embodying the invention has a two-step operation brought about by the construction of the program carrier, which two-step operation is achieved in a particularly simple but reliable manner.

Afte this tattooing operation a further tattooing operation can be rapidly carried out by inserting a further program carrier. Owing to the design of the program carrier, which can no longer be used after one tattooing operation and cannot be made re-usable by the operator, a particularly reliable, tamper-proof tattooing system is obtained, which allows tattooing large numbers of animals within a short time.

Figure 4:
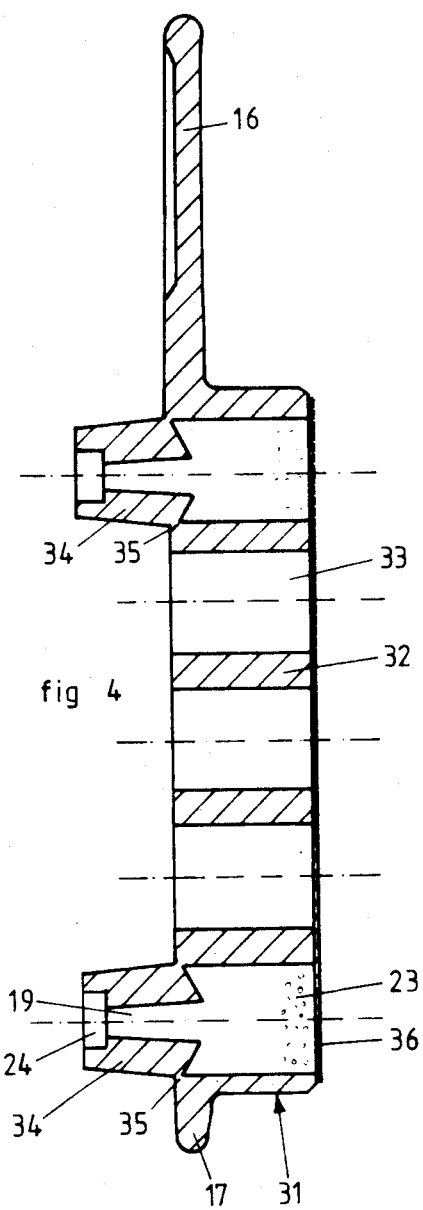

In the embodiment shown in FIG. 4 a program carrier can be provided in a simple manner with pistons. A program carrier 31 comprises a 3×5 matrix of tubular elements 32 and cavities 33. Various parts corresponding to the preceding embodiment are designated by the same reference numerals. In this case also a number of cavities are bounded by a closing element formed by a piston 34. The main difference from the preceding embodiment resides in that the pistons 34 are initially integral with the further part of the carrier 31 and are connected only by a relatively thin peripheral element 35 with the axial end of the cavity. Therefore, the pistons can be sprayed integrally with the carrier, the pistons not required for the symbol being punched away. By the open structure of the cavities 33 on the side of the base plate fluid can be readily added, after which the assembly of cavities 33 are closed at this axial end by a foil 36. Instead of using the foil 36, a plate can be used for the closure, said plate having burls jamming in the cavities 33, by which burls the cover plate is fixed to the base plate.

In the embodiment of FIG. 5 a program carrier 26 is provided with a 3×5 matrix assembly of tubular elements 27 with cavities 28, each of which forms a reservoir having an inner diameter matching the diameter of the coupling part 6 of the needle 2. The cavities 28 are closed on one side by a closing element in the form of a foil 29 made from an appropriate synthetic resin, for example, polypropylene and connected with the carrier 26 by a suitable method, for example, ultrasonic welding. The carrier 26 comprises a base plate 30, which closes, like in the first embodiment, a plurality of cavities 28 as a bottom and does not close other cavities at which the bottom is, for example, removed. During this operation the foil can be punched away at the same time at these cavities.

After the introduction into the pressure element 25 the program carrier 26 operates generally like the carriers of the preceding embodiments. The difference is that in this embodiment the needle 2 with the coupling part 6 itself functions as a piston in the reservoir after the needle has, by the sharp end of the coupling part 6, stretched and subsequently pierced the foil 29 at the area concerned owing to the increase in the force exerted by the pressure element 25. After being stretched the foil 29 ensures by its sealing relationship to the needle that no fluid can escape.

Figure 6:
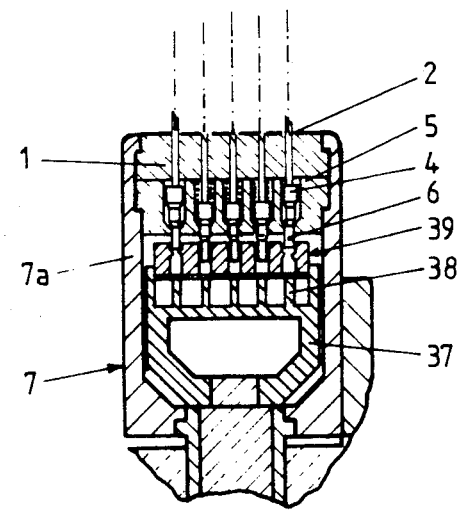
Figure 7:
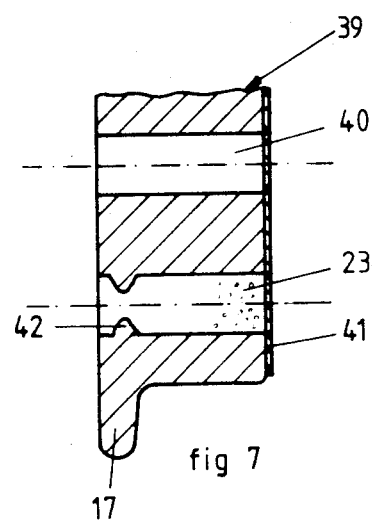

The embodiment shown in FIGS. 6 and 7 illustrates how the piston function can also be performed on the other side of the program carrier opposite needles 2. For this purpose the jaw 7 comprises a pressure plate 37 carrying an assembly of pistons 38, which register with cavities 40 of the program carrier after the latter is introduced into pressure element 25. All cavities 40 are closed after the introduction of fluid 23 by a foil 41 having the function of a closing element and near the other axial end the cavities have internally a narrowed part 42 serving as a stop for the end of the coupling part 6 of the needle 2. When programming the carrier 39 the narrowed parts 42 are removed from the inoperative cavities, during which operation the foil 41 is also pierced at said cavities.

After the program carrier 39 is introduced into the pressure element 37 the pistons 38 move into contact with the foil 41. Subsequently, only the needles corresponding to the symbol to be tattooed are coupled with the narrowed parts 42, said needles penetrating into the tissue. This position of the tattooing device is shown in FIG. 6. Upon exertion of a heavier force by means of the pressure element 37 the pistons 38 penetrate into the closed cavities 40 so that the foil 41 is stretched at the area concerned and the fluid is pressed out of the cavity towards the needle. A number of pistons 38 can move freely through the non-closed cavities and the axial dimension of the cavity is such that each inoperative piston remains by its end at a distance from the end of the coupling part 6 of the needle 2 registering with the piston concerned.

The invention not only relates to the embodiments described and illustrated but also to all variants thereof.

For example, it is possible to fix a plurality of symbols, for example four or eight by a plurality of cavity matrices. Moreover, the tattooing devices embodying the invention enables tattooing fixed symbols rather than changing symbols. For this purpose a needle carrier with only a matrix of needles corresponding to the symbol concerned can be employed. By causing said needles to co-operate with a program carrier composed in the manner described above the two-stage operation of the device according to the invention is also obtained in this situation.

Further, it is possible to employ a program carrier according to the first embodiment (see FIG. 3), with pistons without the shoulder 20, which pistons having an outer diameter slightly larger than the inner diameter of the cavities 13. During a tattooing operation the resistance of the pistons in the cavities in combination with the counter-pressure of the fluid in the cavities is sufficient to penetrate the tissue with the free ends of the needles owing to the force, exerted on the program carrier.

What we claim is:

1. A tattooing device for marking animals by the device of a contrasting fluid into tissue of the animal, said device comprising:
   a needle carrier;
   a plurality of hollow needles carried by said needle carrier, said needles being arranged in a matrix capable of forming marking symbols from combinations of selected ones of said needles, said needles being movable with respect to said needle carrier to an extended position for insertion into the tissue of the animal;
   an exchangeable program carrier having a plurality of cavities containing the contrasting fluid and alignable with selected ones of said needles; and
   operating means receiving said needle carrier and program carrier for relatively moving said program carrier and needle carrier toward and away from each other;
   said cavities containing the contrasting fluid being at least partly closed by a closing element, the movement of said program carrier and said needle carrier toward each other bringing said needles into abutment with said program carrier to extend said selected ones of said needles for insertion in the tissue of the animal to be marked, said closing elements being at least partially deformable by the relative movement of said program carrier and needle carrier for injecting the contrasting fluid from said cavities through said extended needles into the animal tissue, the deformation of the closing elements requiring a greater force than that required to insert the needles into the animal tissue.

2. A tattooing device as claimed in claim 1 wherein said program carrier includes at least one cavity not provided with a closing element.

3. A tattooing device as claimed in claim 1 wherein said closing elements are formed as pistons for said cavities containing the contrasting fluid, said pistons being abuttable with said selected ones of said needles when said program carrier and needle carrier are moved toward each other for extending said needles, each of said pistons having an internal fluid channel alignable with one of said needles and an external deformable peripheral element by which the piston is positioned across the cavity, deformation of said peripheral element permitting movement of said piston into the cavity for pressing the fluid out of the cavity.

4. A tattooing device as claimed in claim 3 wherein said pistons are integrally formed with the program carrier through a deformably breakable connection of the peripheral element to the program carrier.

5. A tattooing device as claimed in claim 3 wherein the peripheral element of said pistons is formed by a shoulder about the exterior of the piston.

6. A tattooing device as claimed in claim 3 wherein at least one of said pistons has a recess surrounding said fluid channel for receiving a needle.

7. A tattooing device as claimed in claim 3 wherein at least one of said pistons has a fluid channel conically narrowing toward the needle.

8. A tattooing device as claimed in claim 1 wherein said closing element comprises a deformable foil-like layer extending across the cavities containing the contrasting fluid.

9. A tattooing device as claimed in claim 8 wherein the cross sectional area of ends of said needles abutting the program carrier corresponds to the cross sectional area of the cavities, said cross sectional areas being taken normal to the direction of needle extension, wherein said foil-like layer is abuttable with said ends of said needles for deformation and perforation, and wherein said ends of said needles act as pistons in said cavities for pressing out the contrasting fluid.

10. A tattooing device as claimed in claim 8 wherein said operating means carries pistons appliable to said foil-like layer and movable in said cavities upon the deformation of said foil-like layer for pressing out the contrasting fluid.

11. A tattooing device as claimed in claim 3 wherein the piston has a greater dimension than the cavity to form the external deformable peripheral element of the piston.

12. A tattooing device as claimed in claim 1 wherein said program carrier has a foil-like layer spanning said cavities for retaining the contrasting fluid in the cavities.

* * * * *